United States Patent [19]

Malchesky

[11] Patent Number: 5,858,305
[45] Date of Patent: Jan. 12, 1999

[54] APPARATUS AND METHOD FOR STERILIZING MEDICAL DEVICES

[75] Inventor: Paul S. Malchesky, Painesville Twp., Ohio 44077

[73] Assignee: Steris Corporation, Mentor, Ohio

[21] Appl. No.: 882,466

[22] Filed: Jun. 25, 1997

[51] Int. Cl.⁶ ..................................................... A61L 2/00
[52] U.S. Cl. ........................... 422/28; 134/93; 134/95.1; 137/268; 422/33; 422/292; 422/300
[58] Field of Search ............................. 422/28, 33, 292, 422/300; 134/166 R, 168 C, 170, 102.2, 93, 95.1; 137/268

[56] References Cited

U.S. PATENT DOCUMENTS

| 4,731,222 | 3/1988 | Kralovic et al. | 422/292 |
|---|---|---|---|
| 4,765,963 | 8/1988 | Mukogawa et al. | 422/68 |
| 5,190,666 | 3/1993 | Bisconte | 210/744 |
| 5,209,909 | 5/1993 | Siegel et al. | 422/37 |
| 5,217,698 | 6/1993 | Siegel et al. | 422/295 |
| 5,225,160 | 7/1993 | Sanford et al. | 422/28 |
| 5,279,799 | 1/1994 | Moser | 422/292 |
| 5,439,654 | 8/1995 | Kochte | 422/292 |

OTHER PUBLICATIONS

"Technical Documentation: Cleaning and Disinfection System for Endoscopes", by Wassenburg & Co. b.v. (Jan. 2, 1997). Drawings only.

Primary Examiner—Krisanne Thornton
Attorney, Agent, or Firm—Fay, Sharpe, Beall, Fagan, Minnich & McKee

[57] ABSTRACT

A decontamination apparatus for medical devices includes a decontamination basin (14a, 14b) with a selectively opened and closed cover member (16a, 16b) to provide selective access to the basin (14a, 14b). A mixing chamber assembly (80) selectively dispenses detergent concentrate and decontaminant concentrate into a liquid to form a liquid cleaning solution or a liquid decontaminant solution, respectively. A source of decontaminated rinse liquid, such as a microbe removal filter (54), is in selective fluid communication with the basin (14a, 14b). A source of anti-microbial liquid is in selective fluid communication with the microbe removal filter (54) and rinse liquid flow paths (58) between the microbe removal filter and the basin for decontaminating the filter (54) and the rinse lines (58). Each channel of a medical device (E) being decontaminated is connected to a channel flush line (30) and a channel pump (32) for flushing the channels of the device (E). A pressure sensor (42) is in communication with each flush line (30) to sense a blockage in the channels of the medical device (E). The channel pumps (32) pump liquid or decontaminated air through the device channels. A leak test system is also provided for testing the integrity of an outer sheath of a medical device (E) such as an endoscope.

20 Claims, 3 Drawing Sheets

APPARATUS AND METHOD FOR STERILIZING MEDICAL DEVICES

BACKGROUND OF THE INVENTION

The present invention relates to the decontamination arts including the sterilization arts. It finds particular application in conjunction with the decontamination of medical devices, especially medical devices such as endoscopes and other devices having channels or lumens that must be decontaminated after use.

Sterilization is typically defined as the absence of all life forms including bacterial endospores which are the living organisms most resistant to known sterilants. Disinfection, by distinction, only connotes the absence of pathogenic life forms. Herein, the general term, decontamination, will be used to describe both disinfection and sterilization.

Endoscopes and similar medical devices having channels or lumens formed therethrough are being used on an ever increasing basis in the performance of medical procedures. The popularity of these devices has led to calls for improvements in the decontamination of these devices between use, both in terms of the speed of the decontamination and the effectiveness of the decontamination. One drawback associated with many known endoscope decontamination devices is their reliance on reusable glutaraldehyde or the like as a liquid decontaminant solution. While glutaraldehyde is generally effective for disinfection, sterilization with glutaraldehyde can take 10 to 12 hours which is too long in today's healthcare facilities. Another drawback to glutaraldehyde systems is that they sterilize without cleaning, i.e., they leave sterile biological waste matter on the medical instruments.

Another drawback associated with many known decontamination devices is their lack of a decontaminated rinse liquid. Many known decontamination devices are concerned only with cleaning and disinfecting the devices and consequently rely on unfiltered "tap" water for rinsing. Even those that filter or otherwise decontaminate the rinse liquid often do not decontaminate the rinse liquid flow paths between the source of rinse liquid and the decontamination basin under the incorrect assumption that these apparently closed rinse liquid flow paths cannot become contaminated. Thus, with these devices, it is possible for microorganisms to be reintroduced onto the medical device from the rinse liquid. One known endoscope sterilizer does provide a sterile rinse and rinse liquid flow path (STERIS SYSTEM 1®, STERIS Corporation, Mentor, Ohio). However, it would be desirable to include additional features in conjunction with the sterile rinse and sterile rinse flow paths of this unit.

Prior medical instrument decontamination devices do not include a simple and effective means for accurately delivering a select charge of both detergent concentrate and decontaminant concentrate as needed to form a cleaning solution and a decontamination solution, respectively. Instead, many prior devices rely upon a large tank to hold a reusable decontaminant such as glutaraldehyde and rely upon tank of detergent that must be refilled. The need to refill these tanks periodically decreases efficiency and also puts an operator in contact with decontaminant and detergent liquid and vapors. Further, glutaraldehyde is an environmentally hazardous material that needs to be chemically deactivated. Disposal or reprocessing of diluted or contaminated glutaraldehyde is inconvenient and costly.

Furthermore, with these systems, it is possible for the detergent tank or the decontaminant tank to run dry without the knowledge of the machine operator. Also, it is not always possible to verify that the detergent or decontaminant has actually been properly and accurately dispensed into the decontamination basin. It would be desirable to provide a decontamination apparatus that simply and accurately dispenses a select dose of detergent concentrate and decontaminant concentrate as needed, without requiring tanks to be refilled and without exposing an operator to detergents and decontaminants. It would also be desirable to provide such a system which reduces the possibility that an incorrect amount of detergent or decontaminant will be dispensed.

The present application is therefore directed to a method and apparatus which overcomes these problems and others while providing better overall decontamination results and efficiency.

SUMMARY OF THE INVENTION

In accordance with one aspect of the present invention, a decontamination apparatus for medical devices is provided. The apparatus includes a decontamination basin with a selectively opened and closed cover member to provide access to the basin. A mixing chamber selectively dispenses detergent concentrate and decontaminant concentrate into a liquid to form a liquid cleaning solution or a liquid decontaminant solution, respectively. A source of decontaminated rinse liquid, such as produced by membrane filtration of microbes, is also provided. Rinse liquid flow paths are located between the microbe removal filter and the basin for supplying decontaminated rinse liquid to the basin. A pump is in fluid communication with the basin such that the liquid decontaminant solution is selectively circulated to the microbe removal filter and rinse liquid flow paths between the microbe removal filter and the basin for decontaminating the filter and the rinse liquid flow paths.

In accordance with another aspect of the present invention, a method of decontaminating a medical device includes positioning the medical device in a basin and circulating a liquid cleaning solution onto the medical device and through channels in the medical device for a select duration to remove residue from the device. An anti-microbial liquid is circulated onto the medical device and through channels in the medical device for a select duration to decontaminate the exterior surfaces and the channels of the device. The anti-microbial liquid is also circulated through rinse liquid pathways to decontaminate the pathways. A decontaminated rinse liquid is supplied onto the medical device and through channels in the medical device. The decontaminated rinse liquid contacts only previously decontaminated pathways.

In accordance with a further aspect of the present invention, an apparatus for sterilizing medical devices includes a decontamination basin for receiving a non-sterile medical device and a plurality of pumps each having an inlet in selective fluid communication with the basin and an outlet for connection with a channel of the medical device such that the liquid from the basin is pumped through the channels of the medical device. A source of sterile air is in selective fluid communication with each pump inlet for pumping sterile air through the medical device channels. At least one spray nozzle is positioned in the basin to spray liquid onto the medical device in the basin and a recirculation pump has an inlet in fluid communication with the basin and an outlet in fluid communication with the at least one spray nozzle for circulating liquid through the basin. A mixing chamber sequentially dispenses (i) a detergent concentrate and, thereafter (ii) a sterilant concentrate into liquid passing through the mixing chamber. A source of sterile rinse liquid includes a microbe removal filter and rinse liquid pathways. The microbe removal filter and rinse liquid pathways are in selective fluid communication with the recirculation pump for communicating liquid sterilant from the basin into the microbe removal filter and through the rinse liquid pathways to sterilize the filter and the pathways.

In accordance with another aspect of the invention, a method of sterilizing the exterior surfaces and interior channels of a medical device includes placing a non-sterile medical device into a basin and mixing detergent concentrate with water to form a cleaning solution. The cleaning solution is circulated over the exterior surfaces and through the internal channels of the medical device in the basin and then drained from the basin. Rinse liquid is circulated over the exterior surfaces and through the internal channels of the medical device in the basin and then drained from the basin. The internal channels of the medical device are flushed with air to remove residual liquid from the channels. Sterilant concentrate is mixed with water to form a liquid sterilant which is circulated over the exterior surfaces and through the internal channels of the medical device in the basin. The liquid sterilant is also circulated into a rinse water microbe removal filter and through rinse liquid pathways between the microbe removal filter and the basin. The liquid sterilant is drained from the basin. Rinse water is passed through the microbe removal filter to sterilize the rinse water. The sterile rinse water is communicated through only previously sterilized rinse liquid pathways onto the medical device in the basin and is circulated over the exterior surfaces and through the internal channels of the medical device in the basin. The sterile rinse water is then drained from the basin.

One advantage of the present invention is that it provides an improved decontamination apparatus and method.

Another advantage of the present invention is that it provides for accurately and conveniently dispensing detergent and decontaminant concentrate ingredients into a liquid to form a cleaning solution or a decontamination solution.

Still another advantage of the present invention resides in the use of a single-use decontaminant.

A further advantage of the present invention is that it provides a decontaminated rinse liquid and decontaminated rinse liquid flow paths for communicating the decontaminated rinse liquid onto and through the channels of the decontaminated medical device.

A further advantage of the present invention resides in its provision of a leak test system for testing the integrity of a sheath or housing forming a part of an endoscope or other device being decontaminated.

A further advantage of the present invention is that it allows each interior flow channel of a medical device to be individually flushed with liquid or decontaminated air and that each interior channel of the medical device can be monitored for blockage.

Yet another advantage of the present invention is the provision of a "break tank" water supply system for isolating the apparatus from a utility or "tap" water supply system.

Still further advantages of the present invention will become apparent to those of ordinary skill in the art upon their reading and understanding of the following specification of the preferred embodiments.

BRIEF DESCRIPTION OF THE DRAWINGS

The invention may take form in various components and arrangements of components and in various steps and arrangements of steps. The drawings are for purposes of illustrating preferred embodiments only, and are not to be construed as limiting the invention.

DETAILED DESCRIPTION OF THE PREFERRED EMBODIMENT

Figure 1:
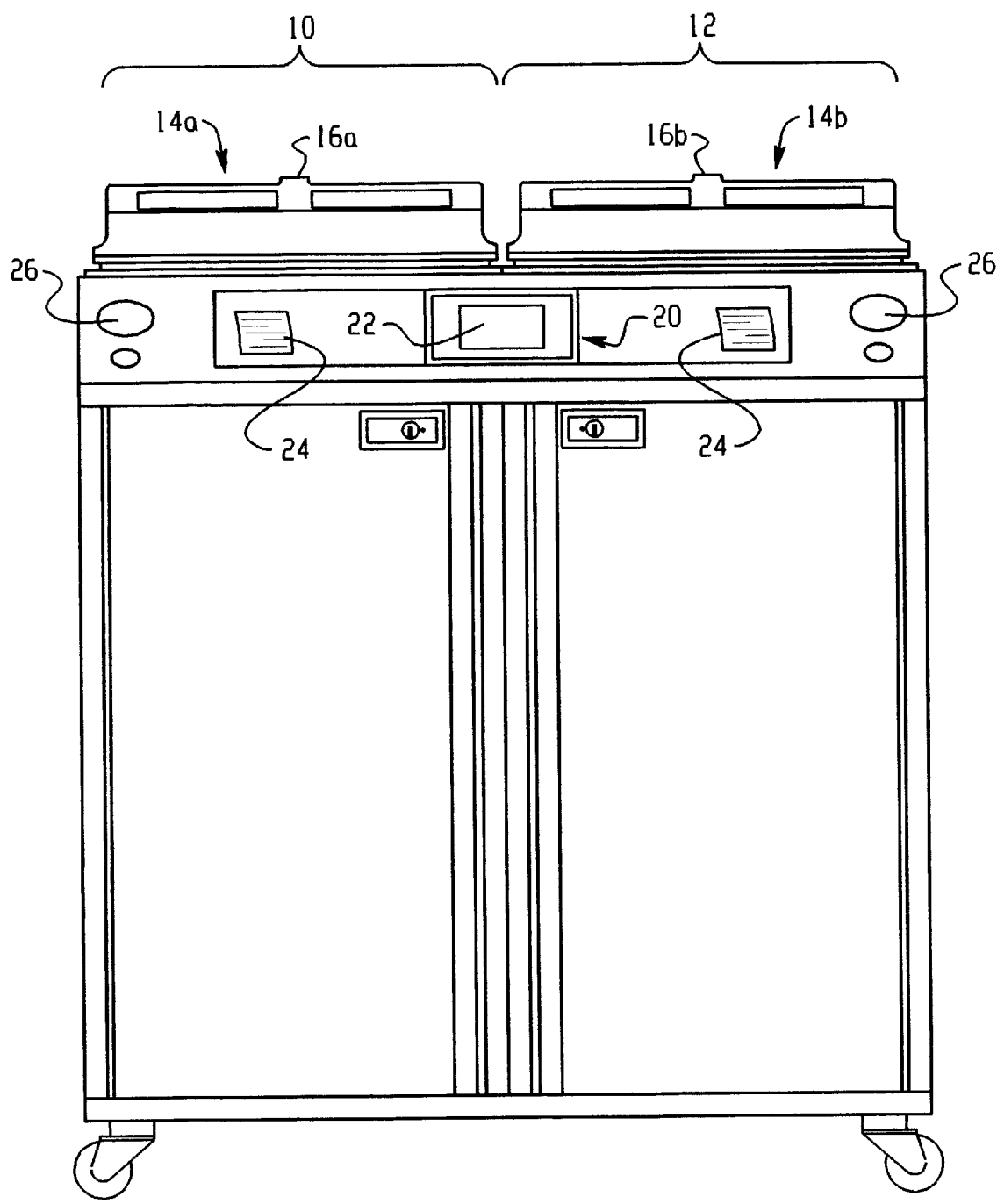
FIG. 1 is a front elevational view of a decontamination apparatus in accordance with the present invention.

FIG. 1 shows a decontamination apparatus for decontaminating endoscopes and other medical devices which include channels or lumens formed therethrough. The decontamination apparatus generally includes a first station 10 and a second station 12 which are at least substantially similar in all respects to provide for the decontamination of two different medical devices simultaneously or in series. First and second decontamination basins 14a, 14b receive the contaminated devices. Each basin 14a, 14b is selectively sealed by a lid 16a, 16b, respectively, preferably in a microbe-blocking relationship to prevent the entrance of environmental microbes into the basins 14a, 14b during decontamination operations. The lids can include a microbe removal or HEPA air filter formed therein for venting.

A control system 20 includes one or more microcontrollers, such as a programmable logic controller (PLC), for controlling decontamination and user interface operations. Although one control system is shown herein as controlling both decontamination stations 10, 12, those skilled in the art will recognize that each station 10, 12 can include a dedicated control system. A visual display 22 displays decontamination parameters and machine conditions for an operator and at least one printer 24 prints a hard copy output of the decontamination parameters for a record to be filed or attached to the decontaminated device or its storage packaging. The visual display 22 is preferably combined with a touch screen input device. Alternatively, a keypad or the like is provided for input of decontamination process parameters and for machine control. Other visual gauges 26 such as pressure meters and the like provide digital or analog output of decontamination or medical device leak testing data.

Figure 2:
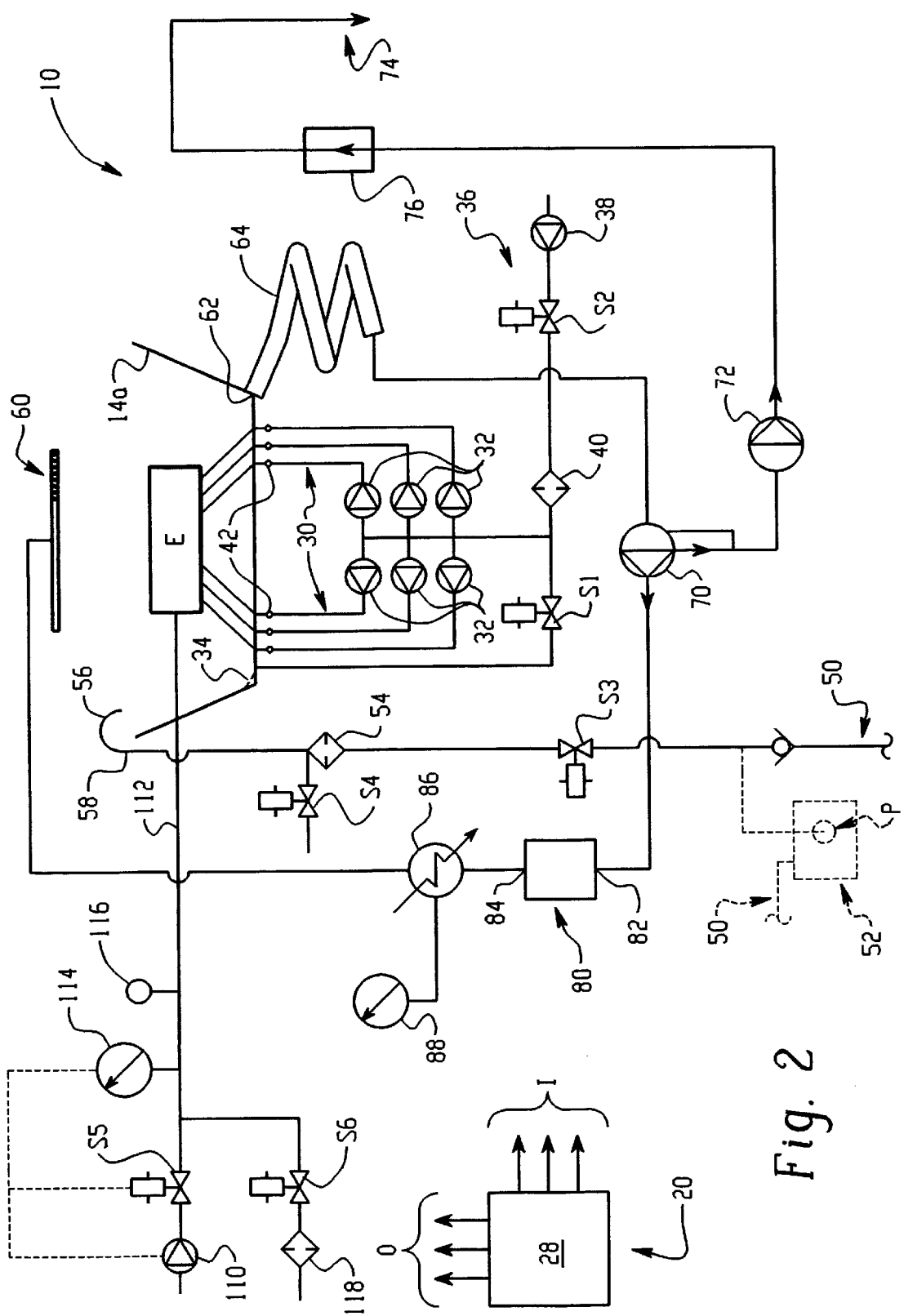
FIG. 2 is a diagrammatic illustration of the decontamination apparatus shown in FIG. 1, with only a single decontamination basin shown for clarity; and, FIG. 3 is an exploded view of a detergent and decontaminant concentrate delivery system in accordance with the present invention.

FIG. 2 diagrammatically illustrates one station 10 of the decontamination apparatus. Those skilled in the art will recognize that the decontamination station 12 is preferably similar in all respects to the station 10 illustrated in FIG. 2. However, the station 12 has not been shown in FIG. 2 for clarity. Further, the decontamination apparatus can be provided with a single decontamination station or multiple stations.

The decontamination basin 14a receives an endoscope E or other medical device therein for decontamination. Any internal channels of the medical device E are connected with flush lines 30. Each flush line 30 is connected to an outlet of a pump 32. The pumps 32 are preferably peristaltic pumps or the like that pump fluid, such as liquid and air, through the flush lines 30 and any internal channels of the medical device E. Specifically, the pumps 32 can either draw liquid from the basin 14a through a drain 34 and a first valve S1, or can draw decontaminated air from an air supply system 36 through a valve S2. The air supply system 36 includes a pump 38 and a microbe removal air filter 40 that filters microbes from an incoming air stream. It is preferable that each flush line 30 be provided with a dedicated pump 32 to ensure adequate fluid pressure and to facilitate the individual monitoring of the fluid pressure in each flush line 30. A pressure switch or sensor 42 is in fluid communication with each flush line 30 for sensing excessive pressure in the flush line. Any excessive pressure sensed is indicative of a partial or complete blockage, e.g., by bodily tissue or dried bodily fluids, in a device channel to which the relevant flush line 30 is connected. The isolation of each flush line 30 relative to the others allows the particular blocked channel to be easily identified and isolated, depending upon which sensor 42 senses excessive pressure.

The basin 14a is in fluid communication with a water source 50 such as a utility or "tap" water connection. A pump is optionally provided to boost the pressure of the water from the utility water connection 50. Alternatively, a "break tank" 52 and an associated pump P provide a source a water which is isolated from the utility connection 50 as is required in certain applications. A valve S3 selectively blocks the flow of utility water into the basin 14a from the source 50. A microbe removal filter 54, such as a 0.2 µm or smaller absolute pore size filter, decontaminates the incoming water which is delivered into the basin through a faucet fixture 56 or the like. A valve S4 selectively allows the decontaminated water to flow through a rotating spray nozzle assembly 60 to spray decontaminated rinse water into the basin 14a and onto the medical device E. The condition of the filter 54 can be monitored by directly monitoring the flow rate of water therethrough or indirectly by monitoring the basin fill time using a float switch or the like. When the flow rate drops below a select threshold, this indicates a partially clogged filter element that requires replacement.

A basin drain 62 drains liquid from the basin 14a. The drain 62 can include an enlarged helical tube 64 into which elongated portions of the medical device E can be inserted if needed to ensure that the device can be accommodated, in the basin 14a. The drain 62 is in fluid communication with a recirculation pump 70 and a drain pump 72. The recirculation pump 70 recirculates liquid from the basin drain 62 to the spray nozzle assembly 60 or otherwise back to the basin to contact the medical device E. The drain pump 72 pumps liquid from the basin drain 62 to a utility drain 74. A flow switch 76 monitors the flow of liquid from the pump 72 to the utility drain 74. The pumps 70,72 can be simultaneously operated such that liquid is sprayed into the basin 14a while it is being drained to encourage the flow of residue out of the basin and off of the device. Likewise, the valves S3 and S4 can be opened while the pump 72 operates to spray decontaminated rinse water into the basin 14a and onto the medical device E during draining operations to provide a better draining of decontaminant or cleaning fluid residue. Of course, a single pump and a valve assembly could replace the dual pumps 70,72.

A mixing chamber assembly 80 includes an inlet 82 in fluid communication with an outlet of the recirculation pump 70. An outlet 84 of the mixing chamber assembly 80 communicates with the spray nozzle assembly 60 through a heating element 86 which selectively heats liquid passing therethrough. A pressure switch or sensor 88 monitors the fluid pressure between the mixing chamber assembly 80 and the spray nozzle assembly 60.

Figure 3:
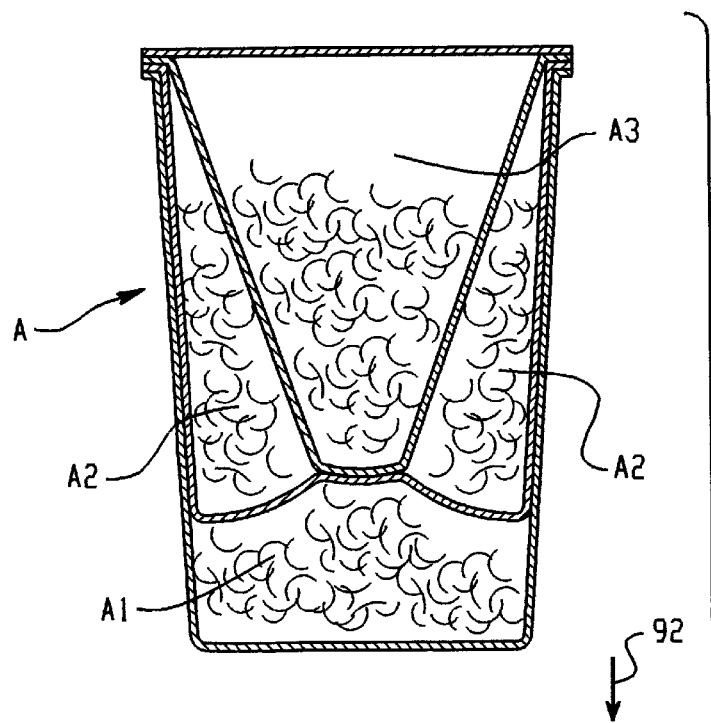
Figure 3:
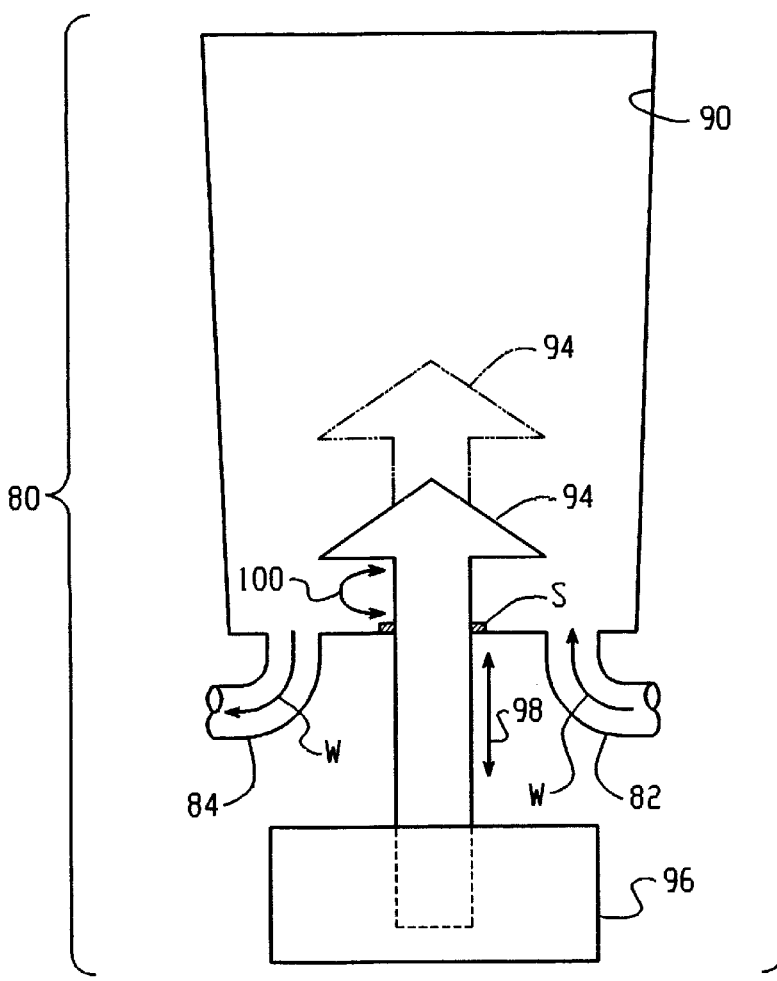

With reference now also to FIG. 3, the mixing chamber assembly 80 includes an ampule receiving chamber 90 that receives an ampule A or an equivalent container. The chamber 90 is preferably positioned for easy operator access in the top surface of the basin 14a and a means is provided for securing an ampule A in the chamber 90. For example, if the chamber 90 is formed in the top surface of the basin 14a, an inner surface of the lid 16a can be utilized to secure an ampule in the chamber 90 when the lid 16a is closed.

The ampule A includes a first interior compartment A1 which contains a detergent concentrate in liquid or dry form. The ampule A also includes second and third interior compartments A2, A3 which contain liquid or dry decontaminant concentrate ingredients. The ampule A is made from a frangible material such as plastic and includes a vented foil, paper, or plastic lid to seal its contents while permitting outgassing. Analogously, releasable panels or other closures can separate and provide selective access to the compartments.

As is indicated by the arrow 92, the ampule A is inserted into the chamber 90. A lance 94 or the like protrudes into the chamber 90 and opens, e.g., pierces, a wall of the first ampule compartment A1 when the ampule is inserted into the chamber 90. In this manner, any water or other liquid flowing through the chamber 90 (indicated by the arrows W) mixes with the detergent concentrate in the compartment A1 to form a liquid cleaning solution. The cleaning solution is optionally heated by the element 86 and is communicated into the decontamination basin 14a through the spray nozzle assembly 60. The liquid cleaning solution is recirculated with the pump 70 through the spray nozzle assembly 60 to clean the exterior of the device E and is recirculated with the pumps 32 to clean any internal channels of the device E. After cleaning, the pump 72 removes the detergent and water mixture. Sterile rinse water sterilized by the filter 54 flushes the detergent and any contaminants resulting from washing operations out of the system. At this point, the pumps 32 are optionally activated along with the opening of the valve S2 and the operation of the air pump 38 to flush sterile air through all channels of the medical device E. This "air rinse" is useful for removing residual sterile water from the channels of the medical device which could undesirably dilute any sterilant subsequently passed through the channels.

In a like manner, the mixing chamber assembly 80 subsequently accesses the second and third interior compartments A2, A3 to introduce decontaminant concentrate ingredients into water, received through the filter 54, in the chamber 90 where the ingredients mix with each other and the water to form liquid decontaminant. A preferred decontamination concentrate is a peracetic acid sterilant concentrate described in U.S. Pat. No. 5,077,008, which is expressly incorporated by reference herein. However, any other suitable decontaminant concentrate can be utilized. The mixing chamber assembly 80 selectively accesses the compartments A2, A3 by advancing the lance 94 further into the chamber 90 (as shown in phantom) to pierce a wall of the compartments A2, A3. An actuator 96, such as one or more solenoids, fluid cylinders, or the like, selectively advances and retracts the lance 94 as indicated by the arrow 98 and optionally rotates the lance 94 as indicated by the arrow 100 to pierce or otherwise access the compartments A2, A3. The decontaminant concentrate in the compartments A2, A3 mixes with clear rinse water or other liquid in the chamber 90 to form a decontaminant solution such as liquid peracetic acid. A seal S prevents liquid flow between the outer surface of the lance and the chamber 90.

Each time decontaminant concentrate is mixed with water or other liquid in the chamber 90 to form the liquid decontaminant, the valve S4 is preferably opened (while the valve S3 remains closed), at least for a select duration, so that liquid decontaminant flows into the microbe removal water filter 54 and the conduit 58 decontaminating the rinse liquid flow paths in their entirety from the filter 54 to the basin 14a. The liquid decontaminant decontaminates the filter 54 and the flow path 58 to ensure that a truly decontaminated rinse liquid is communicated into the basin 14a and onto the device E.

After the decontamination cycle, the pump 72 drains the decontaminant solution and a sterile rinse is again introduced through the filter 54. Once any decontaminant residue is flushed from the device E, the air pump 38 and the pumps 32 are again activated to pump sterile air, sterilized by the filter 40, through channels in the device E to blow out any trapped liquid. Optionally, the sterile air can be used for partially or for fully drying the device.

Endoscopes and other reusable medical devices often include a flexible outer housing or sheath surrounding the individual tubular members and the like that form the interior channels and other parts of the device. This housing defines a closed interior space which is isolated from patient tissues and fluids during medical procedures. It is important that the sheath be maintained intact, without cuts or other holes that would allow contamination of the interior space beneath the sheath. Therefore, the decontamination apparatus includes means for testing the integrity of such as sheath.

An air pump, either the pump 38 or another pump 110, pressurizes the interior space defined by the sheath of the device through a conduit 112 and a valve S5. Optionally, a HEPA or other microbe removing filter removes microbes from the pressurizing air. An overpressure switch 114 prevents accidental overpressurization of the sheath. Upon full pressurization, the valve S5 is closed and a pressure sensor 116 looks for a drop in pressure in the conduit 112 which would indicate the escape of air through the sheath. A valve S6 selectively vents the conduit 112 and the sheath through an optional filter 118 when the testing procedure is complete.

In addition to the input and output devices described above, all of the electrical and electromechanical devices described are operatively connected to and controlled by the control system 20. Specifically, the switches and sensors 42,76,88,114,116 provide input I to the microcontroller 28 such as a PLC. The PLC 28 receives the input I and controls the decontamination and other machine operations in accordance therewith. For example, the PLC 28 includes outputs O that are operatively connected to the pumps 32,38,54,70, 72,110, the valves S1-S6, the mixing chamber assembly actuator 94, and the heating element 86 to control these devices for effective decontamination and other operations.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus for decontaminating medical devices, the apparatus comprising:

a decontamination basin including a selectively opened and closed access member providing access to the basin to receive devices;

a source of decontaminated rinse liquid including a microbe removal filter;

rinse liquid flow paths between the microbe removal filter and the basin for supplying the decontaminated rinse liquid to the decontamination basin;

a mixing region which receives a multi-compartment ampule which holds a charge of a detergent concentrate in a first compartment and a charge of decontaminant concentrate in a second compartment;

a plunger at least partially disposed in the mixing region which moves to (i) a first position for opening the first compartment to dispense the charge of detergent concentrate into a liquid in the mixing region, the plunger stopping at the first position while detergent concentrate mixes with the liquid to form a liquid cleaning solution, and (ii) a second position for opening at least the second compartment for mixing decontaminant concentrate contained therein with a liquid in the mixing region to form a decontaminant solution; and, a pump in fluid communication with the mixing region, the basin, and the rinse liquid flow paths for (1) circulating the cleaning solution through the basin to clean the basin and received devices, and (2) circulating the liquid decontaminant solution to the microbe removal filter and through the rinse liquid flow paths between the microbe removal filter and to the basin for decontamination of the basin and received devices, the microbe removal filter, and the rinse liquid flow paths.

2. The decontamination apparatus as set forth in claim 1 further including:

a microcontroller for controlling the pump and the plunger such that sequentially: (i) the plunger moves to the first position and stops, (ii) the pump circulates the cleaning solution to the basin, (iii) the plunger advances to the second position, and, (iv) the pump circulates the decontaminant solution, and, at least one of a visual display and a printer operatively connected to the microcontroller to provide output of decontamination parameters to an operator of the decontamination apparatus.

3. The decontamination apparatus as set forth in claim 1 further including:

a spray nozzle assembly positioned in the decontamination basin, the spray nozzle assembly being in fluid communication with the pump for spraying the cleaning solution and the decontaminant solution onto a device received in the decontamination basin.

4. The decontamination apparatus as set forth in claim 3 further including means for selectively flushing fluid through channels in a medical device being decontaminated in the basin.

5. An apparatus for cleaning and decontaminating devices, the apparatus comprising:

a decontamination basin in which a device with a plurality of channels is received for decontamination;

a mixing chamber for selectively dispensing a detergent concentrate and a decontaminant concentrate into a liquid to form a liquid cleaning solution and a liquid decontaminant solution, respectively;

a source of decontaminated rinse liquid including a microbe removal filter;

rinse liquid flow paths between the microbe removal filter and the basin for supplying the decontaminated rinse liquid to the basin;

a pump in fluid communication with the basin such that the liquid decontaminant solution is selectively circulated to the microbe removal filter and through the rinse liquid flow paths between the microbe removal filter and the basin for decontamination of the microbe removal filter and the rinse liquid flow paths;

means for selectively opening a multi-compartment ampule which holds both a select charge of the detergent concentrate in a first compartment and the decontaminant concentrate in a second compartment to mix one of the detergent concentrate and the decontaminant concentrate with the rinse liquid to form the liquid cleaning solution and the decontaminant solution, respectively;

a spray nozzle assembly positioned in communication with the decontamination basin, wherein the spray nozzle assembly is in fluid communication with at least a source of liquid decontaminant for spraying liquid decontaminant onto a device in the decontamination basin; and, a means for selectively and independently flushing fluid through the channels in a medical device being decontaminated in the basin, the flushing means including a plurality of channel pumps each having an inlet in fluid communication with the decontamination basin and an outlet for connection with an individual channel of the device in the basin to recirculate liquid from the decontamination basin independently through each individual channel in the device.

6. The decontamination apparatus as set forth in claim 5 further comprising:

a source of decontaminated air, each of the plurality of channel pumps being in selective fluid communication with the source of decontaminated air for circulating decontaminated air through the channels of the device connected in fluid communication therewith.

7. An apparatus for decontaminating devices comprising:

a decontamination basin;

a mixing chamber for selectively dispensing a detergent concentrate and a decontaminant concentrate into a liquid to form a liquid cleaning solution and a liquid decontaminant solution, respectively;

a source of decontaminated rinse liquid including a microbe removal filter;

rinse liquid flow paths between the microbe removal filter and the basin for supplying the decontaminated rinse liquid to the basin;

a pump in fluid communication with the basin such that the liquid decontaminant solution is selectively circulated to the microbe removal filter and through the rinse liquid flow paths between the microbe removal filter and the basin for decontamination of the microbe removal filter and the rinse liquid flow paths;

a means for selectively opening a multi-compartment ampule which holds a select charge of the detergent concentrate in a first compartment and a select charge of the decontaminant concentrate in a second compartment to selectively mix one of the detergent and the decontaminant concentrate with liquid to form the liquid cleaning solution and the decontaminant solution, respectively, wherein the means for opening the ampule includes a plunger movable between a first position for opening the first ampule compartment to dispense the charge of detergent concentrate into a liquid in the mixing chamber, and a second position for opening at least the second ampule compartment for mixing decontaminant concentrate contained therein with a liquid in the mixing chamber;

a plurality of channel pumps for selectively and independently flushing fluid through channels in a device being decontaminated in the basin, each channel pump having an inlet in fluid communication with the decontamination basin and an outlet for connection with an individual channel of the device in the basin to recirculate liquid from the decontamination basin independently through the channels in the device;

a source of decontaminated air, each of the plurality of channel pumps being in selective fluid communication with the source of decontaminated air such that decontaminated air is selectively circulated through the channels of the device; and, a plurality of pressure sensors, each sensor being in fluid communication with one of the channel pump outlets for individually sensing fluid pressure at each channel pump outlet.

8. The decontamination apparatus as set forth in claim 7 further including a means for testing the integrity of a sealed interior area of the device in the basin.

9. The decontamination apparatus as set forth in claim 8 wherein the integrity testing means includes:

a source of pressurized air in selective fluid communication with the sealed interior area of the device in the basin and a pressure monitor for monitoring pressure of the air in the sealed interior area.

10. A method of decontaminating a biologically contaminated device, the method comprising:

(a) positioning the biologically contaminated device in a basin;

(b) opening a first interior compartment of a container to release a select dose of cleaning concentrate into a liquid to form the cleaning solution;

(c) circulating the liquid cleaning solution onto the biologically contaminated device and through channels in the biologically contaminated device for a select duration to remove biological residue from the device;

(d) draining the cleaning solution from the basin;

(e) opening at least a second interior compartment of the container to release a select dose of anti-microbial concentrate into a liquid to form an anti-microbial liquid;

(f) circulating the anti-microbial liquid onto the device and through the channels in the device for a select duration to kill microbes on exterior surfaces and in the channels of the device;

(g) circulating the anti-microbial liquid through rinse liquid pathways to decontaminate the rinse liquid pathways;

(h) draining the anti-microbial liquid; and, (i) supplying a microbially decontaminated rinse liquid through the decontaminated pathways to the device and through channels in the device to remove any cleaning solution and antimicrobial liquid residues.

11. The decontamination method as set forth in claim 10 further including, after step (i):

(j) supplying decontaminated air through the channels in the device to remove residual rinse liquid from the channels.

12. The decontamination method as set forth in claim 11 further including, after step (j):

(k) communicating a pressurized fluid into a sealed interior area of the device; and, (l) monitoring the pressure of the fluid in the sealed interior area of the device.

13. The decontamination method as set forth in claim 12 further including, after step (c):

(c1) circulating a sterile rinse liquid onto the device and through the channels in the device;

(c2) draining the sterile rinse liquid from the basin; and, (c3) circulating sterile air through the channels in the device to remove residual rinse liquid from the channels.

14. The decontamination method as set forth in claim 10 wherein the at least second compartment includes second and third compartments containing separate ingredients which react in water to form the antimicrobial solution, wherein the second and third compartments are accessed together to mix the ingredients with water to form the anti-microbial solution.

15. The method as set forth in claim 10 wherein step (g) includes contacting a rinse liquid microbe removal filter with the anti-microbial liquid.

16. The decontamination method as set forth in claim 10 further including printing a hard-copy output of decontamination process parameters.

17. The decontamination method as set forth in claim 10 wherein the anti-microbial liquid includes peracetic acid.

18. A method of microbially decontaminating a medical device comprising:

(a) positioning the medical device in a basin;

(b) opening a first interior compartment of a container to release a first component to form a liquid cleaning solution;

(c) circulating the liquid cleaning solution onto the medical device and through channels in the medical device for a select duration to remove residue from the device;

(d) opening at least a second interior compartment of the container to release a second component to form an antimicrobial liquid;

(e) circulating the anti-microbial liquid onto the medical device and through the channels in the medical device for a select duration to decontaminate exterior surfaces and the channels of the device;

(f) circulating the anti-microbial liquid through rinse liquid pathways to decontaminate the rinse liquid pathways;

(g) supplying a decontaminated rinse liquid onto the medical device and through channels in the medical device, the decontaminated rinse liquid contacting only the previously decontaminated pathways, including passing water through a microbe removal filter to remove microbes from the water to form the decontaminated rinse liquid; and, (h) monitoring the rate at which the water passes through the microbe removal filter to monitor the condition of the filter.

19. An apparatus for sterilizing a biologically contaminated device including internal channels, said apparatus comprising:

a decontamination basin for receiving a biologically contaminated device;

a plurality of pumps each having an inlet in selective fluid communication with the basin and an outlet for connection with an internal channel of the device such that liquid from the basin is pumped through the channels of the device;

a source of sterile air in selective fluid communication with each pump inlet for pumping sterile air through the device internal channels;

at least one spray nozzle positioned in the basin to spray liquid onto the device in the basin;

a recirculation pump having an inlet in fluid communication with the basin and an outlet in fluid communication with the spray nozzle for circulating liquid through the basin;

a mixing chamber for sequentially dispensing (i) a detergent concentrate and, thereafter (ii) an antimicrobial concentrate into liquid passing through the mixing chamber, the mixing chamber receiving an ampule including a first interior compartment holding a charge of detergent concentrate and at least a second interior compartment holding a charge of antimicrobial concentrate;

a means for sequentially opening the first compartment to form a detergent solution, and subsequently opening the at least second interior compartment of the ampule to form an antimicrobial solution, the mixing chamber being connected with the pumps and the basin for first delivering the detergent solution to clean the device and the internal channels and subsequently deliver the antimicrobial solution to kill microbes remaining on the cleaned device and in the cleaned internal channels.

20. A method of sterilizing the exterior surfaces and interior channels of a medical device, the method including:

(a) placing a non-sterile medical device into a basin;

(b) mixing detergent concentrate with water to form a cleaning solution by opening a first compartment of a multi-compartment ampule to dispense the detergent concentrate into the water;

(c) circulating the cleaning solution over the exterior surfaces and through the internal channels of the medical device in the basin;

(d) draining the cleaning solution from the basin;

(e) circulating a rinse liquid over the exterior surfaces and through the internal channels of the medical device in the basin;

(f) draining the rinse liquid from the basin;

(g) flushing the internal channels of the medical device in the basin with air to remove residual liquid from the channels;

(h) mixing sterilant concentrate with water to form a liquid sterilant by opening at least a second compartment of the multi-compartment ampule to dispense the sterilant concentrate into the water;

(i) circulating the liquid sterilant over the exterior surfaces and through the internal channels of the medical device in the basin;

(j) circulating the liquid sterilant into a rinse water microbe removal filter and through the rinse liquid pathways between the microbe removal filter and the basin;

(k) draining the liquid sterilant from the basin;

(l) passing rinse water through the microbe removal filter to sterilize the rinse water and communicating the sterile rinse water through only the previously sterilized rinse liquid pathways onto the medical device in the basin;

(m) circulating the sterile rinse water over the exterior surfaces and through the internal channels of the medical device in the basin; and, (n) draining the sterile rinse water from the basin.

* * * * *